(12) United States Patent
Laughlin et al.

(10) Patent No.: US 11,741,561 B2
(45) Date of Patent: Aug. 29, 2023

(54) RESCUE OPERATIONS FOR PODS THAT DEPLOY FROM A VEHICLE

(71) Applicant: The Boeing Company, Chicago, IL (US)

(72) Inventors: Brian Dale Laughlin, Wichita, KS (US); John William Glatfelter, Kennett Square, PA (US)

(73) Assignee: THE BOEING COMPANY, Arlington, VA (US)

( * ) Notice: Subject to any disclaimer, the term of this patent is extended or adjusted under 35 U.S.C. 154(b) by 532 days.

(21) Appl. No.: 16/778,519

(22) Filed: Jan. 31, 2020

(65) Prior Publication Data
US 2021/0241404 A1   Aug. 5, 2021

(51) Int. Cl.
| | |
|---|---|
| G06Q 50/26 | (2012.01) |
| H04W 4/90 | (2018.01) |
| H04W 4/029 | (2018.01) |
| G16H 40/63 | (2018.01) |
| B64D 1/00 | (2006.01) |
| B64D 1/08 | (2006.01) |

(52) U.S. Cl.
CPC ............ *G06Q 50/26* (2013.01); *B64D 1/00* (2013.01); *B64D 1/08* (2013.01); *G16H 40/63* (2018.01); *H04W 4/029* (2018.02); *H04W 4/90* (2018.02)

(58) Field of Classification Search
None
See application file for complete search history.

(56) References Cited

U.S. PATENT DOCUMENTS

| | | | |
|---|---|---|---|
| 2,388,380 | A | 11/1945 | Bathurst |
| 2,697,569 | A | 12/1954 | Westcott, Jr. |
| 3,101,919 | A | 8/1963 | Madon |
| 3,423,121 | A | 1/1969 | Lipkin |
| 3,767,253 | A | 10/1973 | Kluetsch |
| 4,664,340 | A | 5/1987 | Jackson |
| 4,699,336 | A | 10/1987 | Diamond |
| 4,890,083 | A | 12/1989 | Trenkler et al. |
| 5,065,162 | A | 11/1991 | Akaba et al. |

(Continued)

FOREIGN PATENT DOCUMENTS

| | | |
|---|---|---|
| RU | 144783 U1 | 8/2014 |
| UA | 88319 U | 3/2014 |
| WO | 2020176415 A1 | 9/2020 |

OTHER PUBLICATIONS

Tucker, P., Why Your Plane Can't Have An Escape Pod, Defense One, Nov. 24, 2015, Retrieved from the internet URL: https://www.defenseone.com/technology/2015/11/why-your-plane-cant-have-escape-pod/123989/ [retrieved on Jan. 31, 2020], pp. 1-5.

(Continued)

*Primary Examiner* — German Viana Di Prisco
(74) *Attorney, Agent, or Firm* — Coats & Bennett, PLLC

(57) ABSTRACT

Methods and devices for monitoring transportation of one or more of travelers and cargo containers in pods that are being transported on a vehicle. The methods and devices may determine that the pods have been deployed from the vehicle. After deployment, the landing locations may be determined. Information may be ascertained about the health of the travelers within the pods and/or a condition of the cargo containers within the pods. Recovery personnel may be notified about this information to facilitate rescue.

20 Claims, 15 Drawing Sheets

(56) References Cited

U.S. PATENT DOCUMENTS

| | | | | |
|---|---|---|---|---|
| 5,356,097 | A * | 10/1994 | Chalupa | B64D 25/12 244/139 |
| 6,382,563 | B1 * | 5/2002 | Chiu | B64D 25/12 244/140 |
| 6,392,538 | B1 * | 5/2002 | Shere | G08B 21/10 340/506 |
| 6,494,404 | B1 * | 12/2002 | Meyer | B64D 25/12 244/118.6 |
| 6,682,017 | B1 * | 1/2004 | Giannakopoulos | B64D 25/12 244/140 |
| 6,965,816 | B2 | 11/2005 | Walker | |
| 7,344,109 | B1 | 3/2008 | Rezai | |
| 9,315,152 | B1 * | 4/2016 | Maestas | G01S 19/13 |
| 9,322,897 | B1 * | 4/2016 | Hoffman | H04B 7/14 |
| 10,303,171 | B1 | 5/2019 | Brady et al. | |
| 10,545,509 | B1 | 1/2020 | Jessen et al. | |
| 11,180,253 | B1 | 11/2021 | Seeley | |
| 11,447,269 | B2 | 9/2022 | Seeley | |
| 2002/0172571 | A1 | 11/2002 | Lawrence | |
| 2005/0247824 | A1 | 11/2005 | Allison | |
| 2006/0079291 | A1 * | 4/2006 | Granovetter | G06F 40/58 704/E15.041 |
| 2006/0219846 | A1 | 10/2006 | Johnson et al. | |
| 2011/0233341 | A1 * | 9/2011 | Monteforte | B64D 25/12 244/140 |
| 2011/0265885 | A1 | 11/2011 | Singh et al. | |
| 2013/0194089 | A1 * | 8/2013 | Estrada | G08B 21/22 340/584 |
| 2014/0160550 | A1 | 6/2014 | Brown et al. | |
| 2014/0231593 | A1 | 8/2014 | Karem | |
| 2014/0302810 | A1 * | 10/2014 | Inha | H04W 4/70 455/556.1 |
| 2015/0266666 | A1 | 9/2015 | Wong | |
| 2015/0351686 | A1 | 12/2015 | Su et al. | |
| 2016/0059963 | A1 | 3/2016 | Burgess et al. | |
| 2017/0057645 | A1 | 3/2017 | Wang | |
| 2017/0124836 | A1 * | 5/2017 | Chung | G08B 25/016 |
| 2017/0251096 | A1 * | 8/2017 | Koepke | B64D 45/00 |
| 2017/0361795 | A1 * | 12/2017 | Del-Fabbro | G07C 5/008 |
| 2018/0086353 | A1 | 3/2018 | Holbrooke et al. | |
| 2018/0170558 | A1 * | 6/2018 | Sapija | B64D 45/00 |
| 2019/0106021 | A1 | 4/2019 | Dietrich et al. | |
| 2019/0176983 | A1 | 6/2019 | Darnell | |
| 2019/0271988 | A1 | 9/2019 | High et al. | |
| 2019/0276129 | A1 | 9/2019 | Morgan | |
| 2020/0047692 | A1 | 2/2020 | Park et al. | |
| 2020/0226892 | A1 * | 7/2020 | Coles | G08B 5/38 |
| 2020/0398730 | A1 | 12/2020 | Glatfelter et al. | |
| 2020/0398731 | A1 | 12/2020 | Glatfelter et al. | |
| 2020/0398732 | A1 | 12/2020 | Glatfelter et al. | |
| 2020/0400437 | A1 | 12/2020 | Glatfelter et al. | |
| 2021/0039766 | A1 * | 2/2021 | Nazhand | B64D 25/12 |
| 2021/0094692 | A1 | 4/2021 | Driscoll et al. | |
| 2021/0183214 | A1 * | 6/2021 | Attariani | H04W 4/02 |

OTHER PUBLICATIONS

Star Wars, Escape Pod, Retrieved from the internet: URL: https://www.starwars.com/databank/escape-pod [retrieved on Jan. 31, 2020], pp. 1-4.

Tablang, K., "This Intriguing Aircraft Concept Aims to Eliminate Airport Lines and Terminals", ForbesLife, Retrieved from the internet: URL:https://www.forbes.com/sites/kristintablang/2016/07/12/clip-air-concept-ecole-polytechnique-ederale-de-lausanne-switzerland/?sh=7421b65a2283 [retrieved on Jun. 17, 2022], Jul. 12, 2016, pp. 1-6.

* cited by examiner

RESCUE OPERATIONS FOR PODS THAT DEPLOY FROM A VEHICLE

TECHNOLOGICAL FIELD

The present disclosure relates generally to the field of transporting one or more of cargo containers and travelers and, more specifically, to the use of pods for the transportation and systems and methods for recovery after deployment from a vehicle.

BACKGROUND

Much of a traveler's time is spent moving from one environment to another. For example, a business traveler that travels from their office to a business meeting in a remote city moves through a number of different environments. This can initially include a first vehicle such as a car or public transportation vehicle to travel from their office to the airport. This can also include the interior of the airport while moving through security and waiting at the airline gate. Another environment includes the one or more aircraft used for traveling to the city where the meeting is located. This can then also include another transportation vehicle to travel from the airport to the meeting.

The traveler is required to physically move into and out of each of these environments during their trip. This includes getting into and out of vehicles, sitting in waiting areas, sitting in the vehicle, moving through security, etc. Further, the traveler is required to closely monitor the time to ensure they are at the correct location at the correct time. This movement and monitoring of time makes it difficult for the traveler to be productive. Further, the required effort can be exhausting to the traveler.

Likewise, cargo containers are often packed and then subsequently repacked multiple times during shipment. For example, a cargo container can be initially packed onto a first vehicle, shipped to a first location, unpacked from the first vehicle at the first location, repacked onto a second vehicle at the first location, and then shipped to a second location. This process continues until the cargo containers are transported to the ultimate destination.

SUMMARY

One aspect is directed to a method of monitoring transportation one or more of travelers and cargo containers in pods that are being transported on a vehicle. The method comprises: determining that the pods have been deployed from the vehicle; determining a location of the pods after landing; determining information about the pods that comprises at least one of a health of the travelers within the pods and a condition of the cargo containers within the pods; and transmitting to recovery personnel the location of the pods and the information about the pods.

In another aspect, the method comprises prioritizing an order of rescue of the pods based on the location of the pods and the information about the pods.

In another aspect, the method comprises prioritizing the order of rescue of the pods based on geographic information about the location of the pods accessed from a source through a wireless communication network in combination with the information about the pods.

In another aspect, the method comprises receiving sensor inputs from the pods and determining the health of the travelers in the pods.

In another aspect, one of the sensor inputs comprises health information received through fitness equipment that is worn by one of the travelers.

In another aspect, the method comprises contacting a utility entity through a wireless communication network and causing power to be disabled at the location prior to the pods landing at the location.

In another aspect, the method comprises transmitting a location of the pods to the other pods after the pods have landed.

In another aspect, the method comprises continuously monitoring the health of the travelers within the pods after the pods have landed.

In another aspect, the method further comprises determining the one or more of the cargo containers contain hazardous materials and creating a rescue priority for the cargo containers with the one or more cargo containers with the hazardous materials being higher on the rescue priority than cargo containers without the hazardous materials.

One aspect is directed to a system to monitor transportation one or more of travelers and cargo containers in pods that are being transported on a vehicle. The system comprises a plurality of pods that each comprise an interior space to house one or more of the travelers and the cargo containers with the pods configured to attach to and be carried by the vehicle. A server is located remotely from the pods and configured to monitor the pods. The server comprises a communication interface and a processing circuit and is configured to: receive signals from the pods through a wireless communication network after the pods have been deployed from the vehicle during transportation; determine information about the pods comprising at least one of a health of each of the travelers in the pods and a condition of cargo containers in the pods; determine a location of the pods; and transmit the information and the location of the pods to remote third parties to facilitate a recovery operation.

In another aspect, canopies are attached to each of the pods with the canopies comprising an undeployed orientation when the pods are attached to the vehicle and a deployed orientation when the pods have been deployed from the vehicle.

In another aspect, the server is further configured to contact a utility entity that supplies a utility to prevent the utility from being supplied to the location while the pods are descending from the vehicle to the location.

In another aspect, the server device if further configured to prioritize an order of rescue for the pods based on the health of the travelers.

In another aspect, the server is further configured to access information through a wireless communication network to determine one or more aspects about the location of the pods.

In another aspect, each of the pods comprise one or more sensors to detect conditions within the interior space with the server configured to determine the health of the travelers within the interior space of the pods based on the conditions.

One aspect is directed to a system to monitor transportation of one or more travelers and cargo containers. The system comprises a plurality of pods that each comprise an enclosed interior space to house one or more travelers and cargo containers with the pods configured to attach to and be carried by the vehicle. A server is located remotely from the pods and is configured to: receive signals from the pods through a wireless communication network after the pods have been deployed from the vehicle; determine a status of the pods after the pods reach a landing location with the status of each of the pods comprising a geographic location of the pod, a number of travelers in the pod, and a health of each of the travelers in the pod; and determine a rescue priority order for each of the pods based on the status of each of the pods.

In another aspect, the server is configured to be accessed by emergency personnel to access the status of each of the pods.

In another aspect, the status of each of the pods further comprises an expected amount of time for emergency personnel to reach the pod.

In another aspect, the server is communicatively coupled to the pods through the wireless communication network.

In another aspect, the pods comprise one or more sensors that detect a condition within the pods and the server configured to determine the health of the travelers in the pod based on the condition detected by the one or more sensors.

The features, functions and advantages that have been discussed can be achieved independently in various aspects or may be combined in yet other aspects, further details of which can be seen with reference to the following description and the drawings.

DETAILED DESCRIPTION

Figure 1:
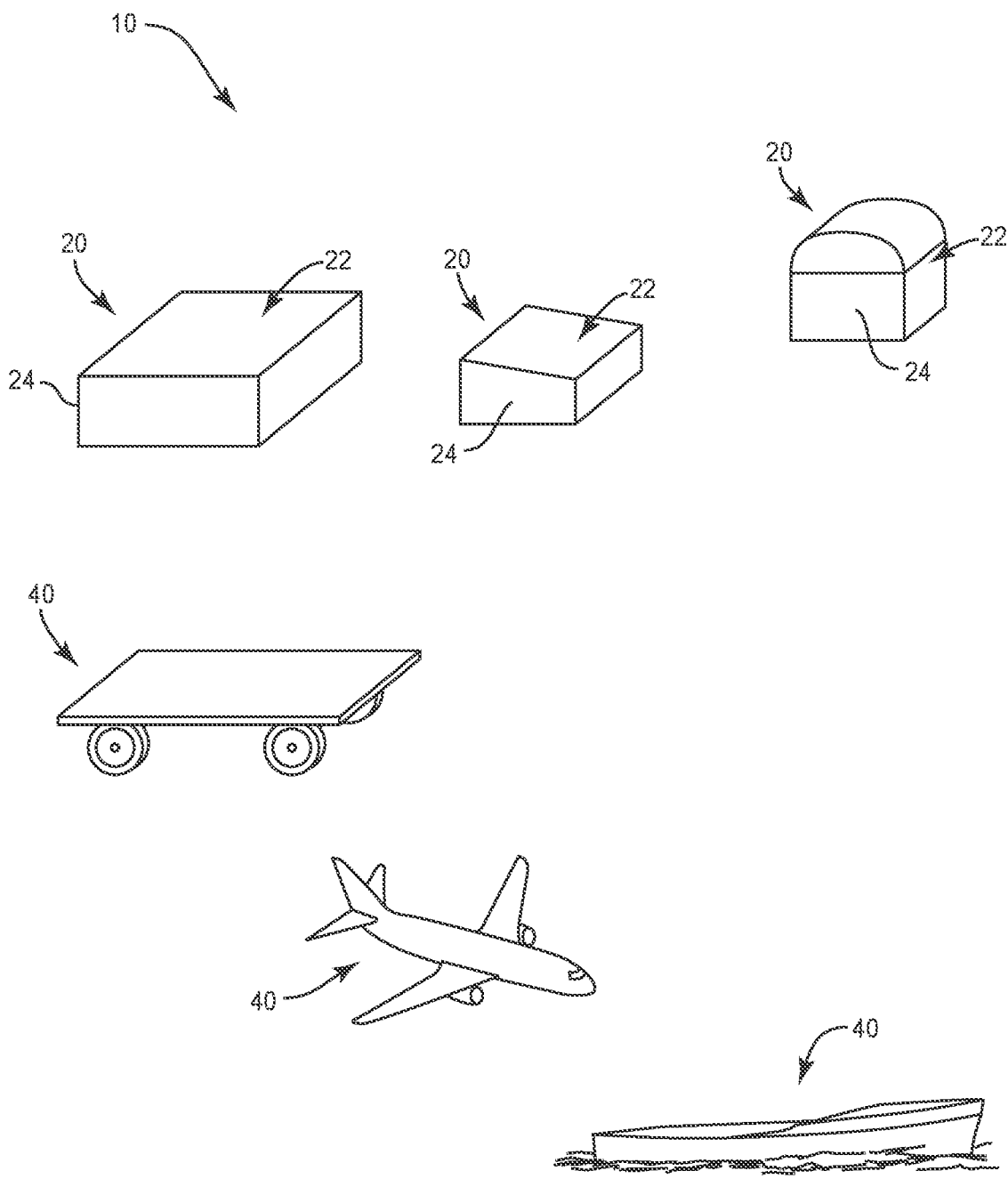
FIG. 1 is schematic diagram of pods that can be attached to an aircraft.

FIG. 1 illustrates a transportation system 10 that includes one or more pods 20. The pods 20 include wall segments 24 that extend around and form an interior space 22 that is configured to house one or more travelers and cargo containers. The pods 20 can be attached to and transported by multiple different vehicles 40. The different vehicles 40 can provide for different modes of transportation. Modes of transportation include but are not limited to ground travel, air travel, water travel, and rail travel. During use, one or more travelers and/or cargo containers are housed within the pod 20. The pod 20 is attached to and transported by one or more vehicles 40 during the travel. For example, the pod 20 can be initially connected to and transported by a land-based vehicle 40 for transportation to an airport. The pod 20 can then be connected to and transported by an air-based vehicle 40 for transportation to a remote destination. During the travel with the two separate vehicles 40, the travelers and/or cargo containers remain within the pod 20 with little to no interruptions that would otherwise occur during the travel.

Figure 2:
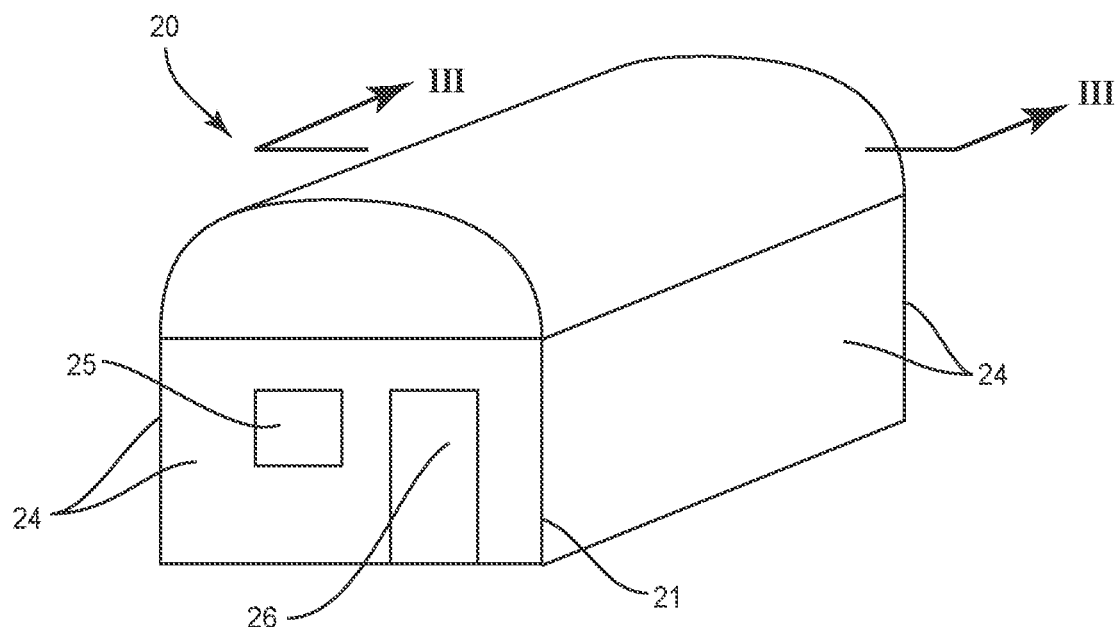
FIG. 2 is perspective view of a pod.

FIG. 2 illustrates a pod 20 that includes a frame 21 with one or more wall segments 24 that can be configured in various shapes and sizes. One or more of the wall segments 24 can be opaque to provide for privacy within the interior space 22. One or more of the wall segments 24 can be translucent to allow light from the exterior to enter into the interior space 22. One or more windows 25 can extend through one or more of the wall segments 24 to allow the travelers to view their environment during travel. One or more doors 26 provide for access into and out of the interior space 22.

Figure 3:
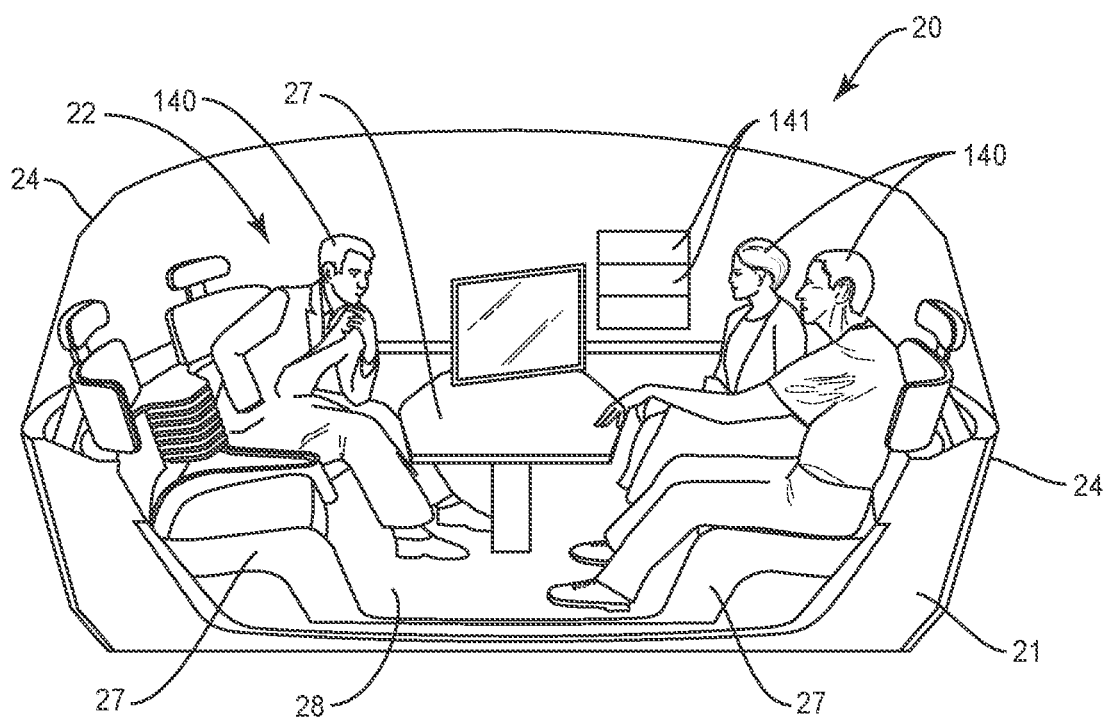
FIG. 3 is a section view of the pod of FIG. 3 cut along line III-III.

FIG. 3 illustrates an interior space 22 configured as a meeting space. Furniture 27 such as chairs, tables, bookshelves, cabinets, and couches are positioned to facilitate the meeting. In one example, one or more of the pieces of furniture 27 are secured to the floor 28. This provides for the furniture pieces 27 to remain upright during movement of the pod 20. This movement can be caused by various forces, such as but not limited to turbulence during flight, and attachment and detachment of the pod 20 with the vehicles 40. In one example, one or more of the furniture pieces 27 remain unattached and are freely movable by the travelers 140 around the interior space 22.

The interior space 22 is designed to facilitate the needs of the traveler 140 during travel. This can include but is not limited the interior space 22 configured as a meeting space during business travel, a bedroom for overnight travel, various general seating arrangements for business and social travel, as an office with one or more desks, a theater arrangement to watch movies during travel, and various other arrangements.

The interior space 22 can also be designed to facilitate the transportation of cargo containers 141. Various shelving, attachment points, etc. can be located to secure the cargo containers 141. Further, the interior space 22 can be temperature controlled. In one example, the interior space 22 is designed to concurrently transport travelers 140 and cargo containers 141. One or more sections can be designed to accommodate travelers 140, and one or more sections are designed to accommodate cargo containers 141. In one specific example, the interior space 22 is divided into a first section for cargo containers 14 land a second section for travelers 140.

Figure 4:
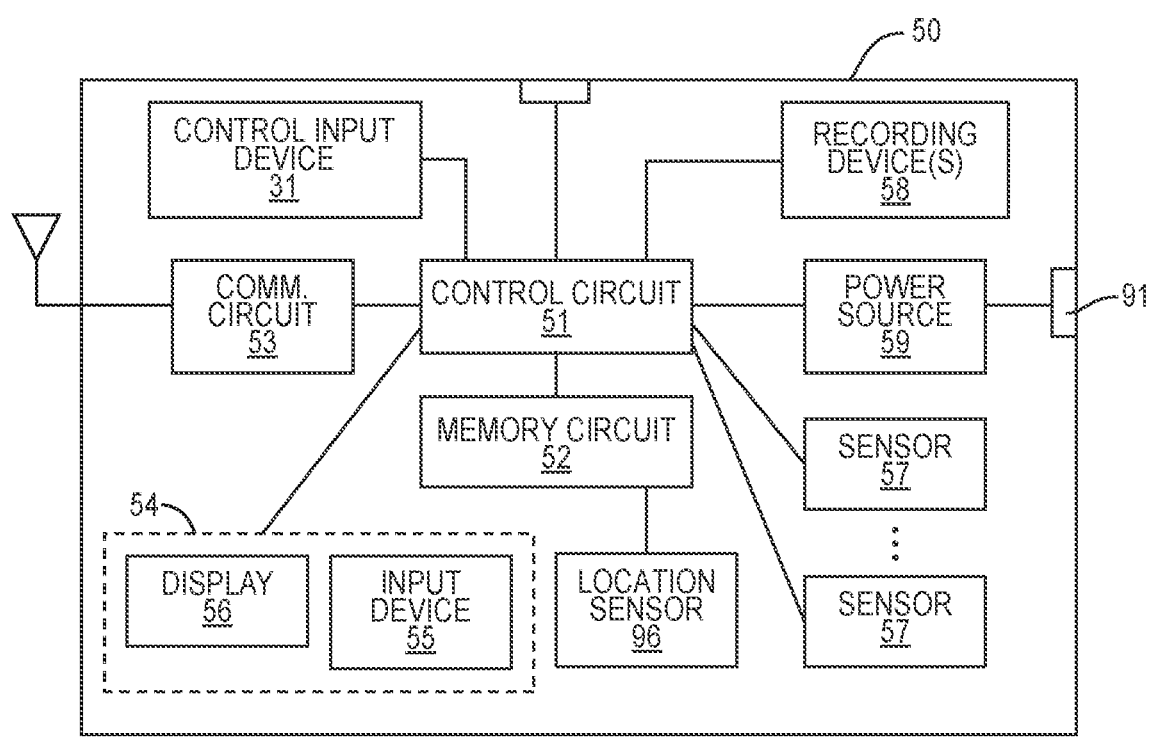
FIG. 4 is a schematic diagram of a control unit of a pod.

The pod 20 includes a control unit 50 as illustrated in FIG. 4. The control unit 50 includes a control circuit 51 and a memory circuit 52. The control circuit 51 controls overall operation of the pod 20 according to program instructions stored in the memory circuit 52. The control circuit 51 can include one or more circuits, microcontrollers, microprocessors, hardware, or a combination thereof. Memory circuit 52 includes a non-transitory computer readable storage medium storing program instructions, such as a computer program product, that configures the control circuit 51 to implement one or more of the techniques discussed herein. Memory circuit 52 can include various memory devices such as, for example, read-only memory, and flash memory. Memory circuit 52 can be a separate component as illustrated in FIG. 4, or can be incorporated with the control circuit 51. Alternatively, the control circuit 51 can omit the memory circuit 52, e.g., according to at least some embodiments in which the control circuit 51 is dedicated and non-programmable.

The control unit 50 is configured to provide for communication functionality for the travelers 140 in the pod 20. Communications can include both incoming and outgoing communications. A communications circuit 53 provides for this communication functionality. The communications circuit 53 enables communication between devices used by the travelers 140 and remote entities over a communication network. The communications circuit 53 can also include one or more devices mounted in the interior space 22 that provide for communications with the remote entities.

The communications circuit 53 can include one or more interfaces that provide for different methods of communication. The communications circuit 53 can include a cellular interface that enables communication with a mobile communication network (e.g., a WCDMA, LTE, or WiMAX network). The communication circuit 53 can include a WLAN interface configured to communicate with a local area network, e.g., via a wireless access point. An exemplary WLAN interface could operate according to the 802.11 family of standards, which is commonly known as a WiFi interface. The communication circuit 53 can further include a personal area network interface, such as a Bluetooth interface. The communication circuit 53 can also include a Near Field Communication interface that provides for short-range wireless connectivity technology that uses magnetic field induction to permit devices to share information with each other over short distances.

In one example as illustrated in FIG. 4, the communications circuit 53 is incorporated into the control unit 50. In another example, the communications circuit 53 is a separate system that is operatively connected to and controlled by the control unit 50.

A user interface 54 provides for a traveler 140 in the pod 20 to control one or more aspects of the pod 20. The user interface 54 can include one or more input devices 55 such as but not limited to a keypad, touchpad, roller ball, and joystick. The one or more input devices 55 provide for the traveler 140 to enter commands to the control circuit 51. The user interface 54 can also include one or more displays 56 for displaying information to the traveler 140. The user interface 54 can also include a communication device that provides for communicating with the remote entities.

One or more sensors 57 detect different aspects of the pod 20. The data from the one or more sensors 57 can be stored in the memory circuit 52. One or more sensors 57 detect the physical condition of the pod 20 such as but not limited to a temperature within the interior space 22, the position of a door 26 of the pod 20 (i.e., open or closed), an orientation of the pod 20, whether the pod 20 is in water, and whether the pod 20 is connected to a vehicle 40. In one example, the one or more orientation sensors 57 detect the orientation as being upright, inverted, or angled. Sensors 57 can also detect aspects concerning the structural integrity of the pod 20, such as when it contacts the ground/water after deployment. These sensors 57 include but are not limited to strain gauges and pressure sensors.

One or more of the sensors 57 can also detect the condition of the travelers 140 within the interior space 22. Examples include movement sensors 57 that detect the movement of the travelers 140, and $CO_2$ sensors to detect carbon dioxide in the interior space 22 to determine whether and/or how much the travelers 140 are breathing.

Another sensor 57 can receive signals from electronic equipment that is worn by the travelers 140. For example, sensors 57 can receive signals from a device that is worn by a traveler 140 (e.g., FITBIT monitor, APPLE watch, GARMIN fitness tracker) that monitors one or more physical aspects of the traveler 140 (e.g., heartbeat, blood pressure, step count).

One or more sensors 57 can detect conditions during a descent of the pod 20 from the vehicle 40. Examples include but are not limited to airspeed, orientation (e.g., altitude, pitch, roll, yawl), and altitude. One or more recording devices 58 can record video and/or audio from within the interior space 22 and/or the space around the exterior of the pod 20.

A location sensor 96 detects the geographic location of the pod 20. Location sensor 96 can include a global positioning system (GPS) component that receives coordinate information from various sources (e.g., satellites, base stations) to determine a geographic position of the pod 20.

A power source 59 provides power to the control unit 50. The power source 59 can include various configurations, including but not limited to batteries. The power source 59 can also provide power to various components that are within the interior space 22, such as a television and lights. One or more solar panels can be mounted on the exterior of the pod 20 and provide recharging to the power source 59. The power source 59 can include a connector 91 to provide a hardwire connection to an external power source (e.g., electrical power from the vehicle 40). FIG. 4 includes the power source 59 incorporated with the control unit 50. In another example, the power source 59 can be separate from the control unit 50 and configured to provide power to the control unit 50.

Figure 5:
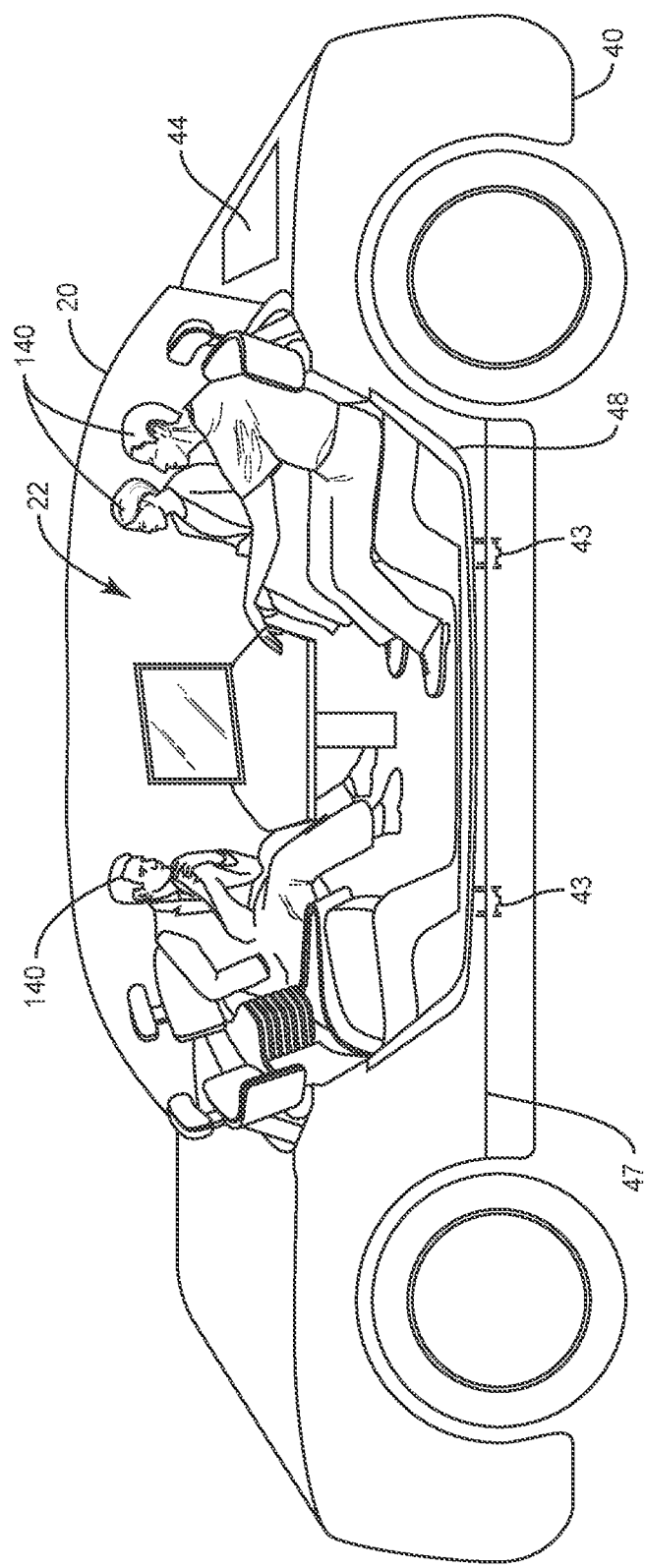
FIG. 5 is a schematic cut-away view of a pod attached to a vehicle.

Various different types of vehicles 40 can connect to and transport the pod 20. One type of vehicle 40 is configured to transport the pod 20 over land. FIG. 5 illustrates an example of a land-based pod 20 that includes a base 47 that supports the pod 20. The base 47 includes a receptacle 48 that receives the pod 20. The vehicle 40 can also include one or more wheels that are driven by an engine 44 for transportation over land. One or more connectors 43 can be positioned at the base 47 to connect to the pod 20. The connectors 43 can provide for a mechanical connection to prevent detachment when the vehicle 40 is transporting the pod 20.

Figure 6:
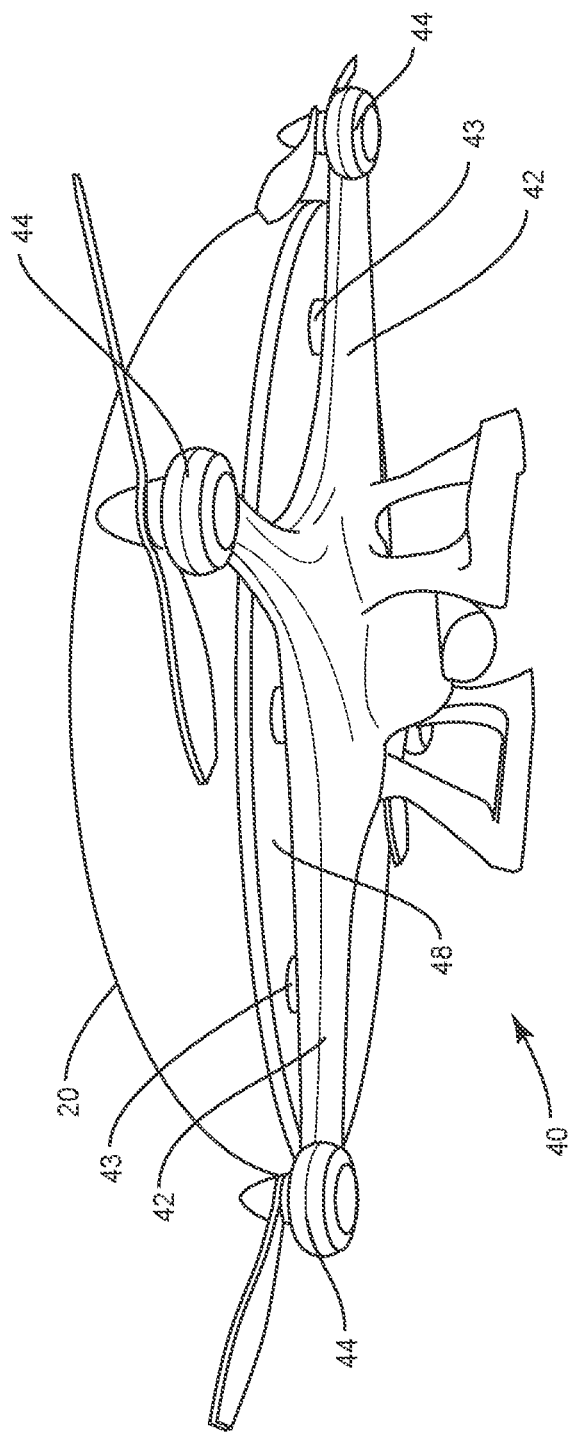
FIG. 6 is a schematic view of a pod attached to a vehicle.

FIG. 6 illustrates a vehicle 40 that provides for air transportation of a pod 20. The vehicle 40 includes a base 47 with a receptacle 48 that receives the pod 20. One or more connectors 43 connect the pod 20 to the base 47. The vehicle 40 also includes wings and engines 44 that provide for flight. In one example, vehicle 40 is configured to be controlled by one or more pilots. In another example, the vehicle 40 is configured for autonomous transportation.

In the various vehicles 40, one or more of the engines 44 can include a propulsion system.

Figure 7:
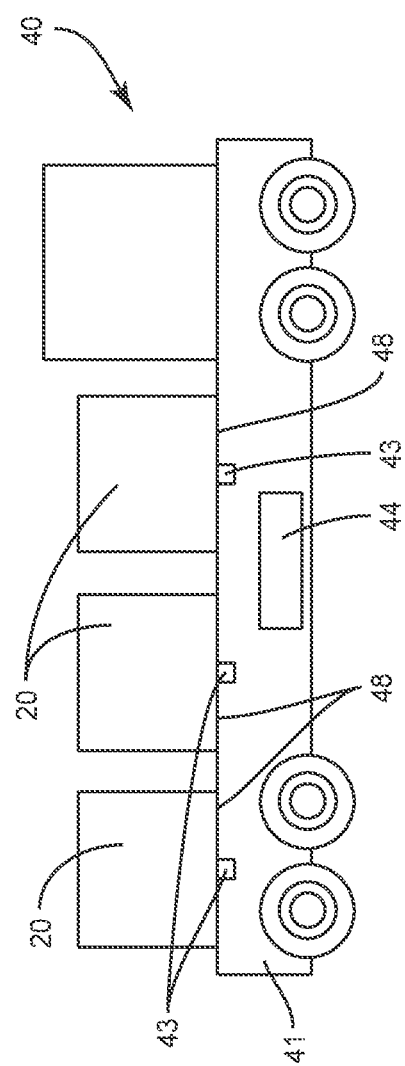
FIG. 7 is a schematic view of pods attached to a vehicle.

The vehicles 40 can be configured to transport a single pod 20, such as the examples of FIGS. 5 and 6. The vehicles 40 can also be configured to transport multiple pods 20. FIG. 7 includes a vehicle 40 with an elongated base 47 with multiple receptacles 48. One or more connectors 43 are positioned at each receptacle 48 to connect the pods 20 to the vehicle 40. The vehicle 40 also includes an engine 44 that drives one or more of the wheels for transportation over land.

Figure 8:
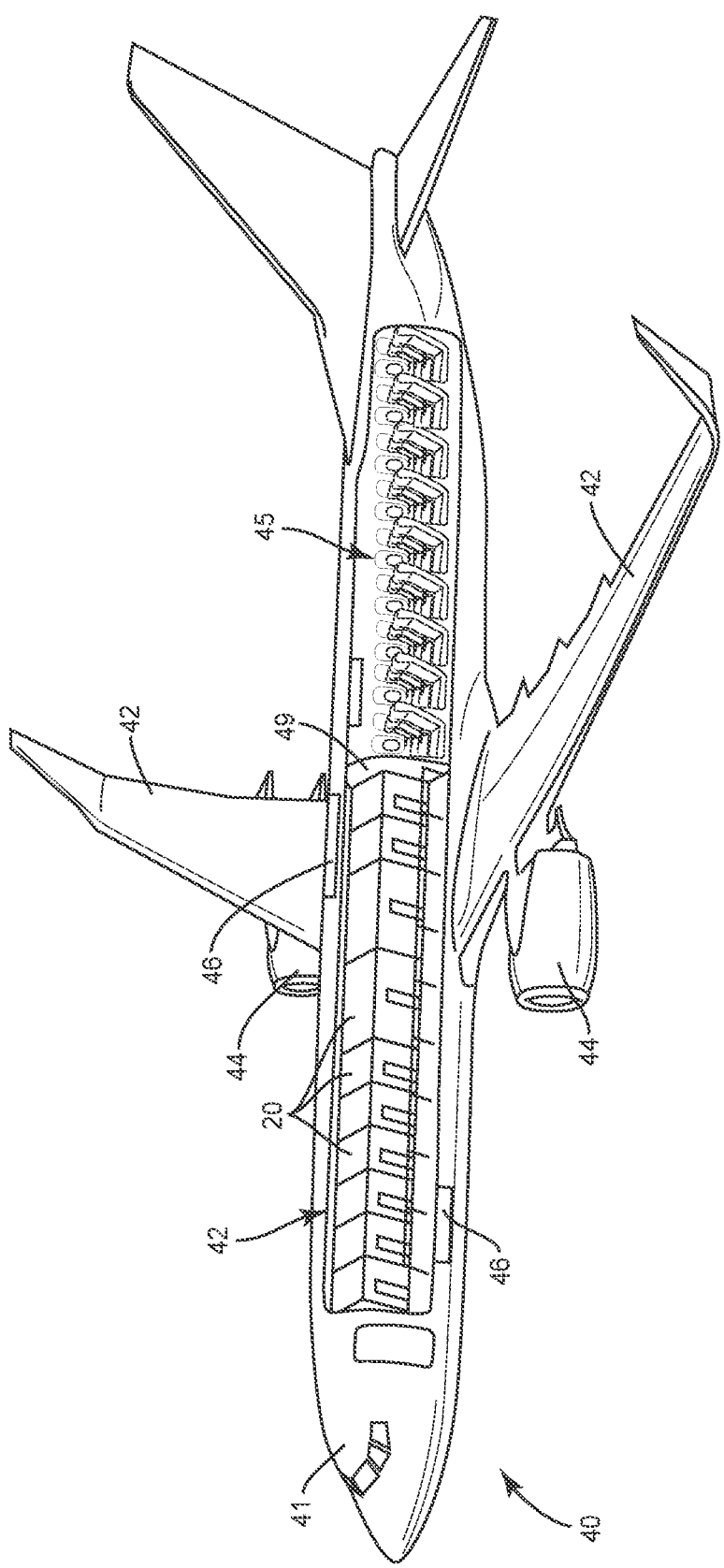
FIG. 8 is a schematic cut-away view of pods positioned within an interior space of an aircraft.

FIG. 8 illustrates a number of pods 20 being transported by a vehicle 40. The vehicle 40 includes wings with one or more engines 44 equipped for flight and a fuselage 41 with an interior space 42 sized to contain the pods 20. The interior space 42 that contains the pods 20 is pressurized to allow travelers 140 to exit the pod 20 during flight (such as to use restrooms or a lounge). The vehicle 40 can also include a cabin area 45 with one or more seats for transporting other travelers. The cabin area 45 can also include one or more lavatories and a galley. The area that contains the pods 20 can be separated from the cabin area 45 by a wall 49. The relative sizes of the section that contains the pods 20 and the cabin area 45 can vary. FIG. 8 includes an example in which each occupies roughly one-half of the area of the interior space 42 of the vehicle 40. Other examples can include the sections having various relative dimensions. In one example, the vehicle 40 is sized to hold a single pod 20.

One or more doors 46 extend into the interior space 42 for loading and unloading the pods 20. The doors 46 can be positioned along one or more different sections of the fuselage 41. The doors 46 can include the same or different shapes and/or sizes and/or configurations. In one example, one or more of the doors 46 are emergency doors 46 for opening if an event were to occur during a flight. One or more of the emergency doors 46 can be opened in various manners, including through the control units 50 of the pods 20, and through a controls unit 120 in the cockpit of the vehicle 40.

Figure 9:
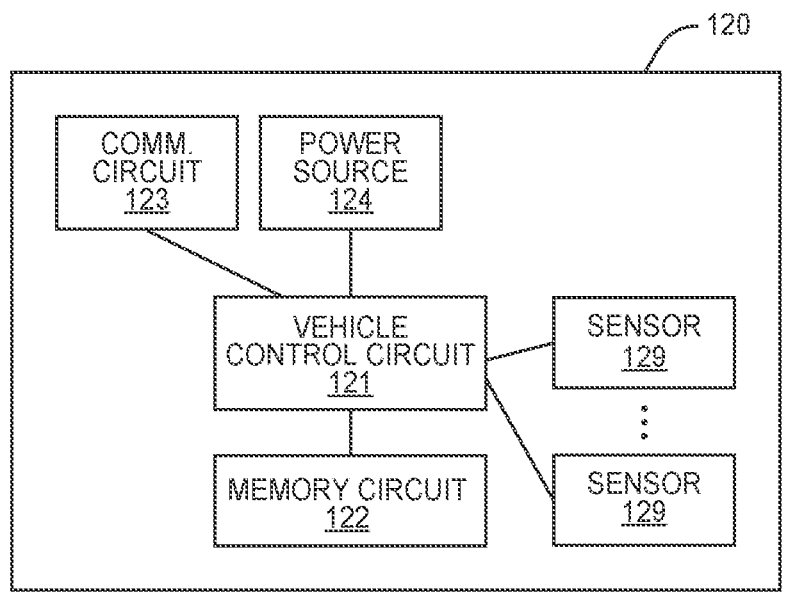
FIG. 9 is a schematic diagram of a control unit of a vehicle.

The various vehicles 40 can include a vehicle control unit 120 to control one or more operations of the vehicle 40. In one example, the control unit 120 is a flight control unit that controls the operation of an aircraft. As illustrated in FIG. 9, the control unit 120 includes a control circuit 121 and a memory circuit 122. The control circuit 121 controls one or more operations of the vehicle 40 according to program instructions stored in the memory circuit 122. The control circuit 121 can include one or more circuits, microcontrollers, microprocessors, hardware, or a combination thereof. Memory circuit 122 includes a non-transitory computer readable storage medium storing program instructions, such as a computer program product, that configures the control circuit 121 to implement one or more of the techniques discussed herein. Memory circuit 122 can include various memory devices such as, for example, read-only memory, and flash memory. Memory circuit 122 can be a separate component, or can be incorporated with the control circuit 121.

A communications circuit 123 provides for communication functionality for the vehicle 40. The communications circuit 123 can provide for different methods of communication, and can include one or more of a cellular interface that enables communication with a mobile communication network, and a WLAN interface configured to communicate with a local area network. In one example, the communications circuit 123 is incorporated into the control unit 120. In another example, the communications circuit 123 is a separate system that is operatively controlled by the control circuit 121. The communication circuit 123 can further include a personal area network interface, such as a Bluetooth interface, and a Near Field Communication interface that provides for short-range wireless connectivity technology that uses magnetic field induction to permit devices to share information with each other over short distances.

One or more sensors 129 provide for detecting one or more conditions with the vehicle 40. Conditions include but are not limited to temperature within the vehicle 40, smoke within the vehicle 40, operation of the engines 44, geographic location, and connection of one or more pods 20. A power source 124 provides power to the control unit 120 as well as components within the vehicle 40. The power source 124 can include various configurations, including but not limited to batteries.

The pod 20 can function as an independent unit when unattached from a vehicle 40 as well as when attached to a vehicle 40. This independence includes the control unit 50 providing the needed functionality to support the travelers 140 and/or cargo containers 141. For example, the control unit 50 can provide for communications to and from the pod 20 through the communications circuit 53. The power source 59 can provide electrical power to the components within the interior space 22, including both components that are integral with the pod 20 (e.g., lights, video equipment) and those brought into the interior space 22 by the traveler 140 (e.g., cellphone, laptop computer). The control unit 50 can also provide control of the interior temperature.

Figure 10:
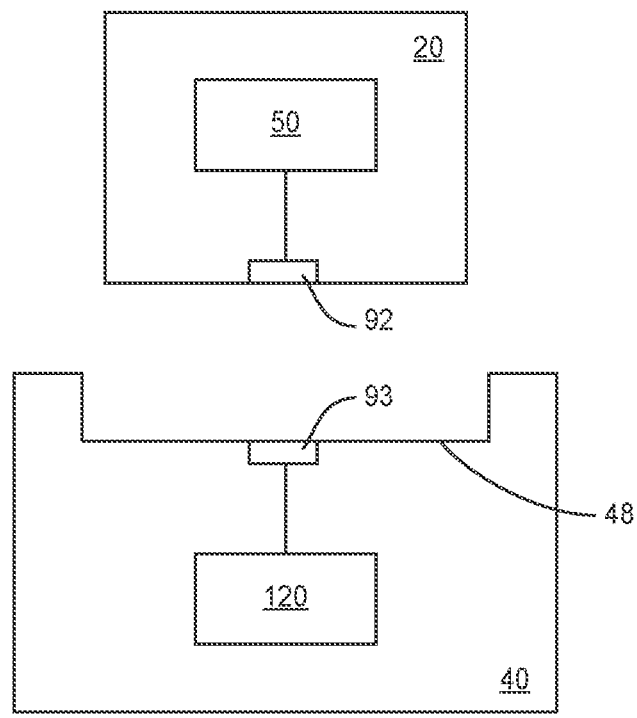
FIG. 10 is a schematic diagram of a pod being connected to a vehicle.

The pod 20 can further be configured to receive one or more of the utility functions from the vehicle 40 when attached to the vehicle 40. FIG. 10 illustrates a manner by which the pod 20 can connect to and receive one or more of the utility functions from the vehicle 40. The pod 20 includes a port 92 that is connected to the pod control unit 50. Likewise, the vehicle 40 includes a port 93 that is connected to the aircraft control unit 120. When the pod 20 is connected to the vehicle 40, the ports 92, 93 engage together to provide for one or more of the utility functions to be supplied from the vehicle 40 to the pod 20.

Figure 11:
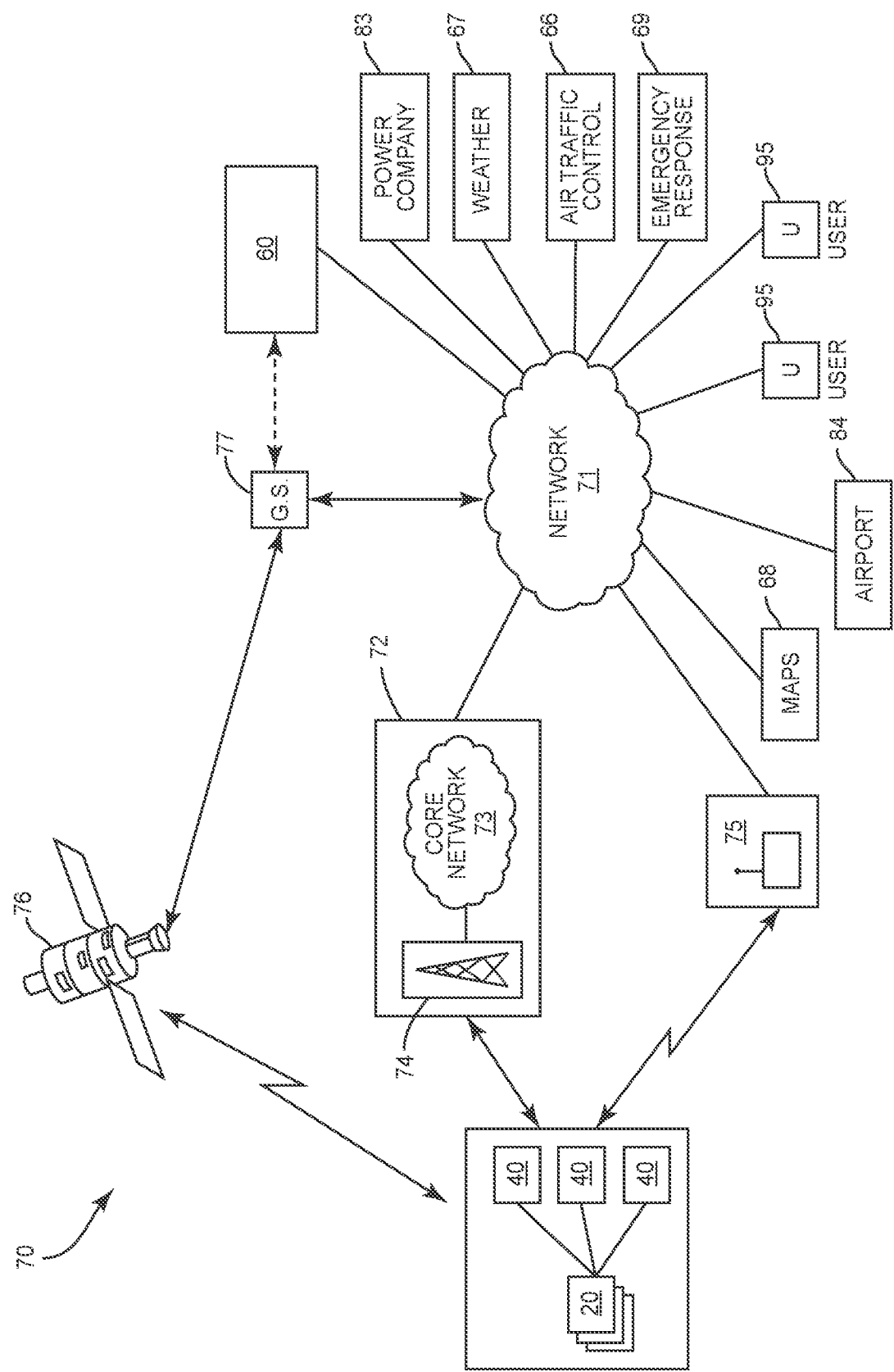
FIG. 11 is a schematic diagram of a wireless communication network.

As illustrated in FIG. 11, a remote server 60 monitors the pod 20 during transportation. The monitoring can occur while the pod 20 is connected to the vehicle 40, as well as when disconnected from the vehicle 40. The remote server 60 monitors and communicates with the pod 20 and vehicle 40 through a wireless communications network 70. The communications circuits 53, 123 of the pods 20 and vehicles 40 respectively enable communication with the server 60 through the wireless communications network 70.

The wireless communication network 70 can includes a packet data network (PDN) 71. The PDN 71 can include a public network such as the Internet, or a private network. The wireless communications network 70 can include a mobile communication network 72 (e.g., a WCDMA, LTE, or WiMAX network). The mobile communication network (MCN) 72 includes a core network 73 and a radio access network (RAN) 74 including one or more base stations. The MCN 72 can be a conventional cellular network operating according to any communication standards now known or later developed. For example, the MCN 72 can comprise a Wideband Code Division Multiple Access (WCDMA) network, a Long Term Evolution (LTE) network, or WiMAX network. The MCN 72 is further configured to access the packet data network (PDN) 71.

The communications circuits 53, 123 can also communicate through a Wireless Local Area Network (WLAN) 75 that operates according to the 802.11 family of standards, which is commonly known as a WiFi interface.

Communications can also be available through one or more satellites 76. The satellites 76 can communicate to the server 60 through one or more of ground stations 77. The ground stations 77 can communicate to the server 60 through the PDN 71, or without use of the PDN 71.

Figure 12:
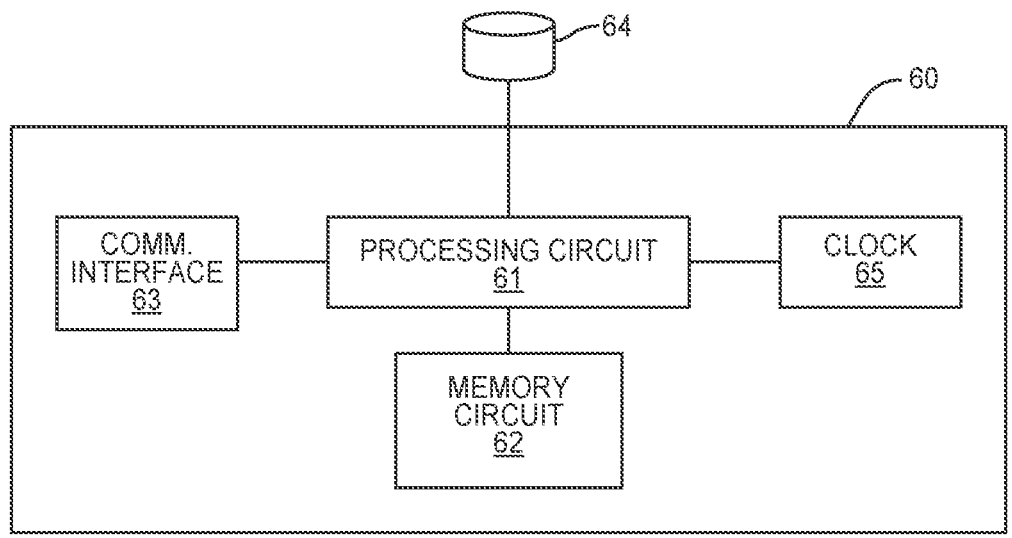
FIG. 12 is a schematic diagram of a server.

As illustrated in FIG. 12, the server 60 includes one or more processing circuits (illustrated as processing circuit 61) that may include one or more microprocessors, microcontrollers, Application Specific Integrated Circuits (ASICs), or the like, configured with appropriate software and/or firmware. A computer readable storage medium (shown as memory circuit 62) stores data and computer readable program code that configures the processing circuit 61 to implement the techniques described above. Memory circuit 62 is a non-transitory computer readable medium, and may include various memory devices such as random access memory, read-only memory, and flash memory. A communications circuit 63 connects the server 60 to the PDN 71, and can be configured to communicate with the PDN 71 according to one or more 802.11 standards. The communications circuit 63 can support a wired connection (e.g., Ethernet), a wireless connection, or both. A database 64 stores information about the travelers 140, cargo containers 141, pods 20, and vehicles 40. The database 64 is stored in a non-transitory computer readable storage medium (e.g., an electronic, magnetic, optical, electromagnetic, or semiconductor system-based storage device). The database 64 can be local or remote relative to the server 60. A clock 65 can measure various timing requirements regarding the transportation of the pods 20. The clock 65 can be incorporated with the processing circuit 61, or can be a separate component independent from the processing circuit 61.

The server 60 can be configured to provide a web interface for access by one or more entities. The server 60 is configured for accessing information about the pods 20, travelers 140, and cargo containers 141 using a browser-based interface or an applications program interface (API). The browser-based interface can include a website through which the contents of the database 64 can be accessible. Although the website can be hosted by the server 60, it can also be hosted at another location accessible through the PDN 71.

Entities can access the information at the server 60 through a variety of devices 95. The devices 95 can include laptop computers, personal computers, personal digital assistants, mobile computing/communication, tablet devices, and various other-like computing devices. Each of the entities uses a respective device 95 and accesses the server 60 through the PDN 71, or alternatively some other network. In one embodiment, one or more of the entities can use his or her respective device 95 to access the server 60 through a separate portal. Each entity's portal can include a secure interface through which the entity can access the information that is assigned to them.

A variety of different entities through their devices 95 can have access to some or all of the information at the server 60. The entities can include travelers 140, owners of cargo containers 141, and various emergency personnel (e.g., police, firefighters, coast guard) responding to an event with the vehicle 40. Entities can also include family members, friends, and business associates that are associated with the travelers 140 and cargo containers 141 and desire to track the status of the transportation.

The server 60 can also access one or more information sources through the PDN 71. Sources can include but are not limited to air traffic control 66, weather 67, maps 68, and emergency response 69 (e.g., fire department, police department).

The entities access the information about the travelers 140 and cargo containers 141 through the server 60. In one example, the server 60 is configured for browser-based accessibility. The browser-based interface can support well-known browsers such as Internet Explorer and Mozilla Firefox, Safari, Chrome. Alternatively, or in conjunction the entities can obtain the information using one or more APIs through their device 95.

Prior to traveling on a pod 20, information about the travelers 140 and cargo containers 141 is entered and maintained at the database stored at the server 60. For a traveler 140, the information can include but is not limited to name, address, age, emergency contact, any health issues, etc. Likewise, information about the cargo containers 141 is entered and stored such as but not limited to identification of the cargo container 141, weight, fire classification (e.g., flammable, combustible), and hazardous material classification.

Information is also maintained for the pods 20 and vehicle 40. For a pod 20, the information can include but is not limited to: year manufactured; size (e.g., weight); safety equipment (e.g., airbags, parachutes, water flotation), independent control features (e.g., autopilot capability to land during a descent); communication ability; on-board emergency equipment; and locator beacon information. For the vehicle 40, the information can include but is not limited to: year manufactured; safety equipment; and utility functions and specifications. The information about the pods 20 and vehicles 40 can be part of the flight record or kept in separate records that are accessible through the server 60.

Figure 13:
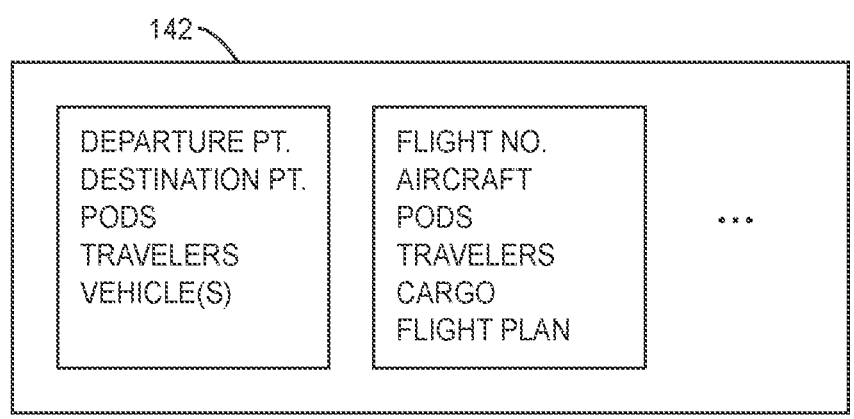
FIG. 13 is a schematic diagram of travel records stored at a server.

Prior to each trip, a travel record 142 is compiled and stored in the database 64. As illustrated in FIG. 13, the travel plan can include departing and destination points, the one or more vehicles 40 that provide transport during the trip, number of pods 20, number of travelers 140 and cargo containers 141 in each pod 20. For a travel record 142 that includes air travel, the flight number can also be included in the travel plan. The specific information previously entered for each traveler 140 and cargo container 141 can be included in the travel record 142, or referenced in a manner to be accessible during the occurrence of an event.

Events can occur during a trip in which the pods 20 are deployed from the vehicle 40. The events cause the one or more travelers 140 and cargo containers 141 in the pods 20 to be safer by deploying than by staying connected to the vehicle 40. Events include but are not limited to a mechanical issue with the engine 44 of a vehicle 40, a fire in the vehicle 40, damage to the vehicle 40 that prevents and/or reduces the ability to operate, and a weather-related issue that affects the vehicle 40. The pods 20 are equipped to protect the travelers 140 and cargo containers 141 during the deployment from the vehicle 40 and landing on the ground and/or water. The pods 20 can also be equipped with supplies to assist the travelers 140 after reaching the ground/water.

Figure 14:
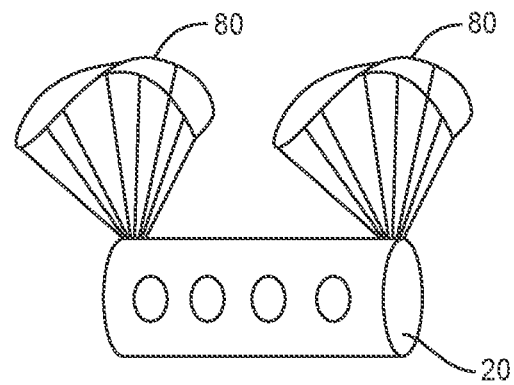
FIG. 14 is a perspective schematic view of pod with a pair of chutes in deployed orientations.

FIG. 14 illustrates one example of a pod 20 equipped for deployment from an aircraft. The pod 20 includes one or more canopies 80 that open during deployment from the aircraft. The canopies 80 provide for a controlled descent from the aircraft and a safe landing. The pod 20 can also include wings (not illustrated) to further facilitate control during the descent. The canopies 80 can be stowed away in a manner that minimizes their size when not in use.

Figure 15:
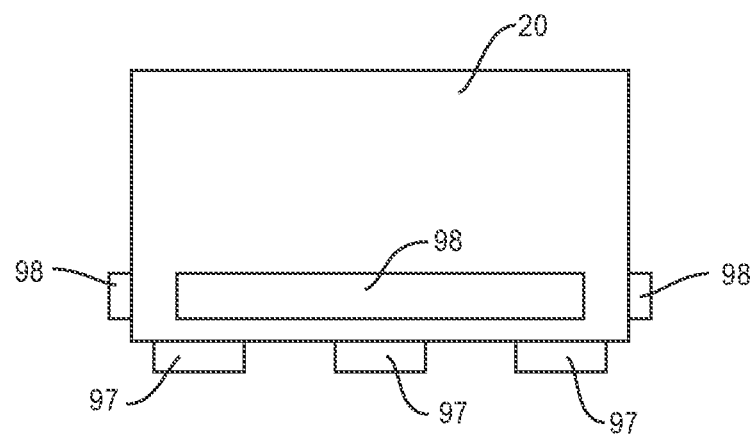
FIG. 15 is a schematic diagram of a pod with air bags and flotation devices.

FIG. 15 includes a pod 20 with one or more airbags 97. The airbags 97 can be mounted in the interior space 22 and/or mounted to the exterior of the pod 20. The airbags 97 can be in a stowed orientation while the pods 20 are in the vehicle 40 to minimize the amount of occupied space. The activation can occur by various manners and at various times. In one example, the airbags 97 are activated when the pod 20 is deployed from the vehicle 40. In another example, the airbags 97 are deployed upon contact with the ground and/or water. In another example, the airbags 97 are deployed based on an input from one or more sensors 57 (e.g., a change in altitude above a predetermined rate, a change in velocity). In one example, activation of the airbags 97 requires a combination of a received pod deploy command from either control unit 50, 120 and a detected condition by a sensor 57.

One or more flotation devices 98 can be attached to the pod 20. The flotation devices 98 are configured to float the pod 20 during a water landing. The flotation devices 98 can also maintain the orientation of the pod 20 in the water, such as to keep a top of pod 20 above the water. The flotation devices 98 can be in a stowed orientation when the pod 20 is within the vehicle 40. Deployment can occur in various situations, including but not limited to when the pod 20 contacts the water, and when the control unit 50 in the pod 20 receives a signal from a sensor 57 that the pod 20 has landed in water.

The server 60 monitors the location of the pod 20. In one example, the server 60 monitors the location after the pod 20 throughout the trip that includes before an event. One or both of the control unit 50 in the pod 20 and control unit 120 in the vehicle 40 periodically transmit signals that include the geographic position of the pod 20. In another example, the server 60 receives the location information from another source through the wireless communication network 70, such as an air traffic controller 66 that monitors the flight.

In another example, the server 60 monitors the geographic location just after deployment of the pod 20 from the vehicle 40. The indication of the deployment of the pod 20 from the vehicle 40 can be received from one or more of the control units 50, 120. In another example, the server 60 monitors readings from one or more sensors 57 on the pod 20. The server 60 is configured to detect a deployment based on the one or more sensor readings. In another example, the server 60 obtains deployment information from a source through the wireless communication network 70 (e.g., air traffic controller source 66).

After the pod 20 has deployed from the vehicle 40, the server 60 monitors the geographic location through signals sent through the control unit 50 on the pod 20. This can include while the pod 20 is still moving after deployment, such as during the descent from an aircraft or while still moving across the ground after deploying from a truck or train. The location information can be obtained through the location sensor 96 on the pod 20. In another example, the server 60 monitors the location by accessing one or more sources (e.g., air traffic controller source 66) through the wireless communication network 70.

The server 60 monitors the location of each of the pods 20 after deployment. The monitoring of each can occur in the same or different manners. In one example, the location of each pod 20 is monitored through location signals received from the pods 20. In another example, the geographic location of the pods 20 is tracked through an information source accessed through the wireless communication network 70. The pod 20 can continue to monitor the geographic position until the recovery operation is complete. This can be particularly useful in situations in which the pod 20 continues to move after deployment, such as after a water landing in which the pod 20 drifts within the water.

The server 60 can determine the expected landing locations for the pods 20 after deployment from the vehicle 40. The landing location can be calculated based on various information including but not limited to the point of deployment, altitude, and forward velocity that is received from the pod 20 and/or vehicle 40. Information can also include data previously stored at the server 60 about the pod 20 such as expected glide path, and weight. The information can also include information obtained from one or more sources through the network 71, such as weather conditions. The server 60 is able to then determine the expected landing site for the one or more pods 20 based on this information. Similar calculations can be obtained in other deployments that can occur during ground (e.g., truck, train) or water (ship) travel.

Figure 16:
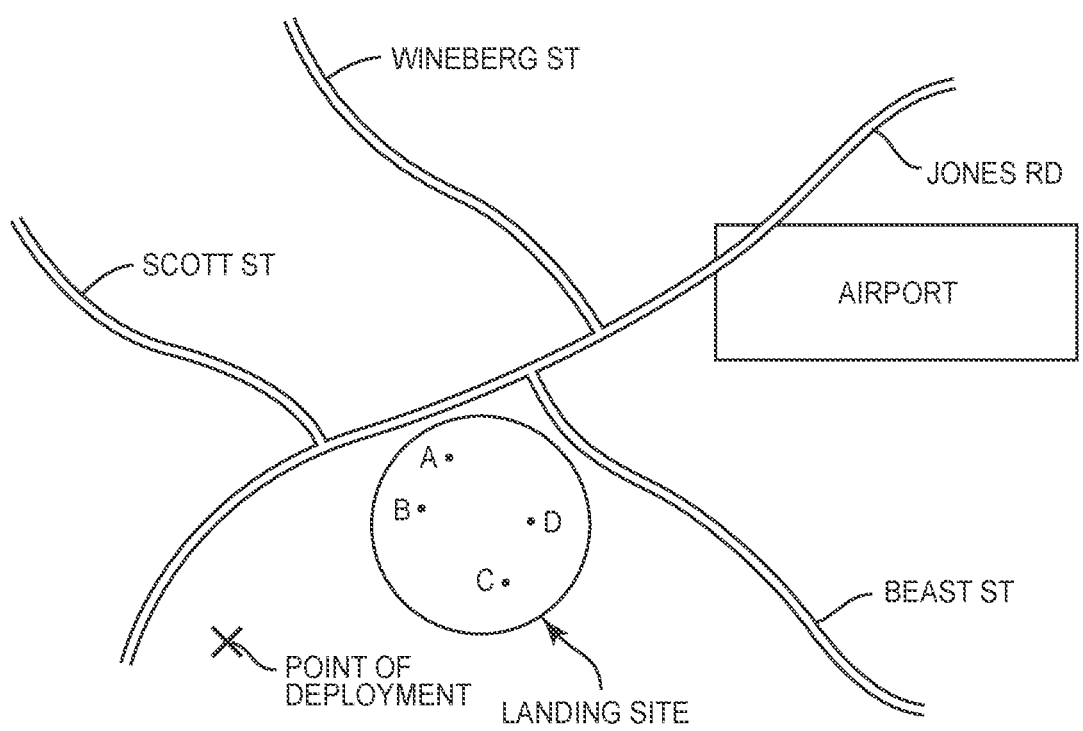
FIG. 16 is a schematic diagram of a map with a point of deployment and a landing site of pods that deploy from a vehicle.

The server 60 can take measures to protect the pods 20 immediately after the deployment. For example as illustrated in FIG. 16, a deployment of multiple pods 20 occurs from an aircraft. The server 60 receives an indication of deployment of the pods 20 and calculates the expected landing site. The server 60 contacts one or more sources to provide for the safety of the pods 20. In one example, this includes contacting a power company 83 through the wireless communication network 70 to shut off power to electrical lines in this area. In another example, this includes contacting the airport 84 and/or air traffic control 66 to divert air traffic around this area. In an example in which deployment occurs from a marine vehicle 40, server 60 can contact the coast guard to notify them of the deployment. The notification of the deployment can cause the coast guard to divert maritime traffic away from the deployment area in the event it is considered dangerous to the pods 20, or alternatively to divert maritime traffic toward the deployment area to assist with rescuing the pods 20. In an example in which deployment occurs from a land vehicle 40, the server 60 can contact the Highway Patrol. This notification can cause the Highway Patrol to close the road on which the pods 20 were deployed. The Highway Patrol can also close other roads in the area to provide for emergency personnel to access the pods 20. Using the example of FIG. 16, the highway patrol could close Beast St. and Jones Rd. as these are in proximity to the landing site. These closures provide access to this area by emergency personnel.

The server 60 monitors the condition of the one or more travelers 140 and cargo containers 141 after the deployment. After determining the occurrence of the deployment, the server 60 can access the records for the pods 20 and the travel record 142. This information can include the number of travelers 140, ages, and if there are any pre-existing medical conditions (e.g., history of heart attacks, asthma). For cargo containers 141, this information can include the contents, whether there are hazmat or fire risks, and whether the contents need to be maintained in a specific temperature range.

The health of the travelers 140 within the pods 20 can be ascertained in various manners. In one example, a traveler 140 in the pod 20 can transmit information about each traveler 140 through the control unit 50. In one example, the control unit 50 and/or server 60 cause a medical questionnaire to be displayed to the traveler on the display 56. The traveler 140 is then able to answer the questions and provide the server 60 with the relevant medical condition of each traveler 140. In another example, the traveler 140 simply notifies the server 60 of any relevant medical emergencies.

The pods 20 can be equipped to determine the condition of the travelers 140 when there is no direct input from one of the travelers. In one example, one or more sensors 57 within the pod 20 are configured to receive signals from electronic equipment that is worn by the travelers 140. For example, sensors 57 can receive signals from a monitoring device that is worn by a traveler 140 (e.g., FITBIT monitor, APPLE watch, GARMIN fitness tracker) that monitors one or more physical aspects of the traveler 140 (e.g., heartbeat, step count, blood pressure).

The medical condition of the travelers 140 can also be based on movement and/or sound within the interior space 22. One or more of the sensors 57 detect movement and sound within the interior space 22. The server 60 determines the medical condition based on the amount of movement and/or amount of noise. In one example, a higher medical condition is determined when no movement or sound is detected, as opposed to a lower level medical condition when movement and/or sound is detected.

One or more sensors 57 can detect carbon dioxide in the interior space 22 to determine the extent of breathing of the travelers 140. The server 60 can use this information in combination with the physical aspects of the interior space 22 (e.g., size of interior space) and number of travelers 140 to determine the medical condition.

Figure 17:
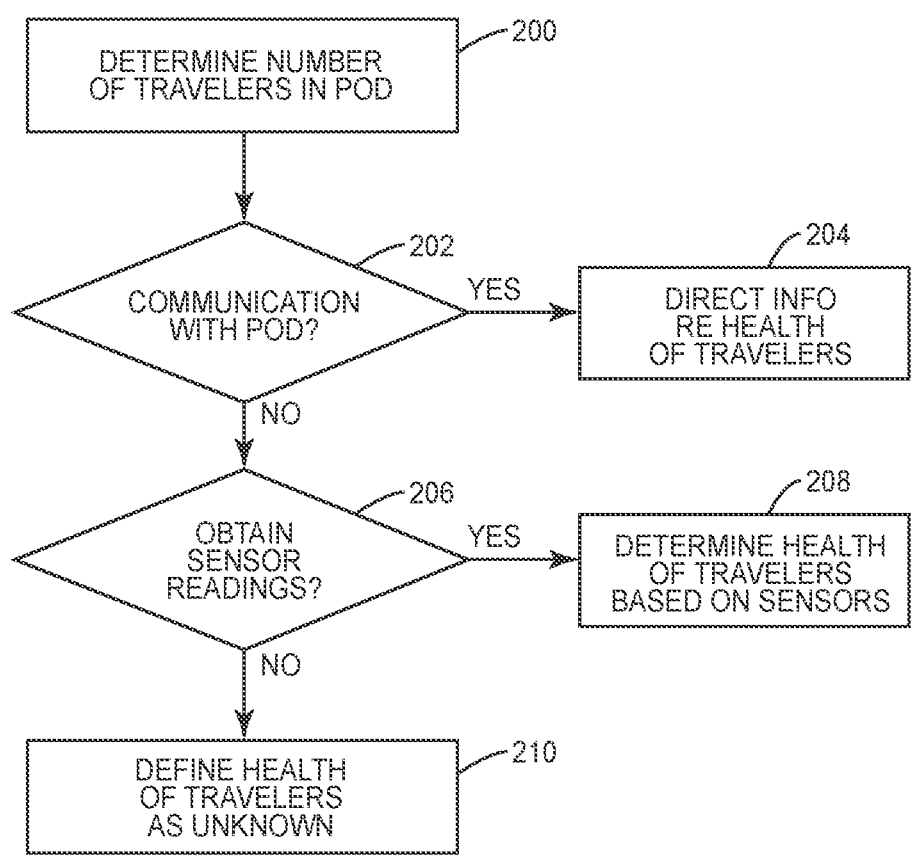
FIG. 17 is a flowchart diagram of a method of determining the medical conditions of the one or more travelers in a pod.

FIG. 17 illustrates a method of determining the medical conditions of the one or more travelers 140 in a pod 20. The server 60 initially determines the number of persons in the pod 20 (block 200). This can include accessing the travel record 142 of the pod 20 that is stored in the database 64. The record 142 can include the number of travelers 140 in the pod 20 and whether there are any pre-existing health issues with the travelers 140. If communications are successful with the pod (block 202), the server 60 can determine the health of the travelers 140 based on the communication (block 204). In one example, the server 60 requests specific health information about each traveler 140. This can include transmitting a status inquiry which is displayed on the display 56 in the pod 20 and provides for the traveler 140 to input the relevant information. In another example, the traveler 140 either inputs information through an input device 55 and or voice communication.

If there is no communication with a traveler 140 in the pod 20 (block 202), the server 60 obtains information from one or more of the sensors 57 (block 206). As stated above, this can include but is not limited to temperature within the interior space 22, $CO_2$ levels, movement, and information obtained from personal equipment worn by the traveler 140s. Sensor readings can also detect the force at which the pod 20 contacted the ground/water. This information is used to determine the health condition of the travelers 140 (block 208). If there is no information available, the travelers 140 health conditions can be listed as unknown (block 210).

The server 60 monitors the health of the travelers 140 until they are rescued by emergency personnel. In one example in which there is communication with a traveler 140 at the pod 20, the server 60 periodically queries the traveler 140 for updated health information. When communications are not available, the server 60 can monitor the one or more sensor readings to maintain a current medical condition for the travelers 140.

In the various examples, the server 60 can rely on a combination of two or more methods to determine the health conditions. For example, the server 60 can rely on information communicated from a traveler 140, as well as information from one or more of the sensors 57.

For each pod 20, the server 60 determines the health condition of each traveler 140. Using the example of FIG. 16 that includes pods A, B, C, and D on the ground at the landing site, the first pod A includes 3 travelers 140 with 2 in critical condition and 1 healthy. The second pod B includes 2 travelers 140 that are both unhurt. The third pod C includes 7 travelers 140 with 2 minor injuries and 5 unhurt. The fourth pod D includes 1 traveler 140 that is unhurt.

The server 60 provides medical instructions to the traveler 140 in the pod 20. This can include information on how to perform various medical processes to provide aid to the travelers 140. Examples include but are not limited to how to apply a bandage, how to suture a cut, how to administer medicine, and how to diagnosis an injury.

The server 60 can also communicate the location of other pods 20 that are nearby. This provides for the travelers 140 to obtain help from other travelers 140 who are in the area, or to provide assistance to the other travelers 140. Using the example of FIG. 16, the server 60 can communicate to pod A the location of pod B that is close proximity. The server 60 can also communicate the location of other nearby features such as roads and buildings.

Upon determining a deployment, the server 60 can access information from one or more sources through the wireless communication network 70. The server 60 can use this information to assist with the rescue operation. A map source 68 can be accessed to analyze the various features of the landing site. Features can include but are not limited to nearby roads, buildings, and geography (e.g., mountains, rivers, lakes, and ravines). The server 60 uses this information to assist with the rescue operation, such as to direct emergency personnel to the landing site.

The server 60 acts as a repository for data about the pods 20, travelers 140, and cargo containers 141. The information is provided or otherwise made accessible to the appropriate authorities. The information can be made available after the deployment, or can be generally available at any time for access by emergency personnel. In one example, the server 60 initially determines the deployment prior to the emergency personnel. This can be due to the direct communication with the pod 20 and/or vehicle 40 at the time of deployment. The server 60 can then be the first to notify emergency personnel of this event and to start the rescue operation. The authorities can then access the information at the server 60 through the PDN 71 or similar manner as described above. Emergency personnel responding to the pods 20 can access the information through user devices 95 while in the field. The server 60 acts as a repository for the information about the deployment and provides a single point of information for persons involved in the rescue.

The server 60 maintains updated information about the pods 20, travelers 140, and cargo containers 141. The updated can be based a variety of manners, including but not limited to communications with one or more of the travelers 140, readings from sensors 57, information obtained from sources, as well as information from emergency personnel. The server 60 can also be configured for rescue personnel to enter information about the rescue. For example, rescue personnel can enter aspects about finding the landing site, such as geography they encounter on traveling towards the landing site, traffic conditions, and weather. Emergency personnel can also enter information once they reach the pods 20, such as health condition of the travelers 140 and condition of the cargo containers 141. In one example, emergency personnel are provided with secure login credentials to enter this information into the server 60. This prevents false information from being entered by mischievous individuals who could be monitoring the rescue operation.

Server 60 can determine an order of rescue of the pods 20. This order can be supplied to emergency personnel who are responding to the rescue operation. The rescue order can be determined based on instructions stored in the memory circuit 62. The order can be based on one or more factors about the travelers 140 and/or cargo containers 141. One factor can include the health of the travelers 140. A traveler 140 in critical condition will have a higher priority than an non-injured traveler 140 or a traveler 140 with minor injuries. Another factor can include the number of travelers 140 in a pod 20. A pod 20 with a larger number of travelers 140 will have a higher priority than a pod 20 with fewer travelers 140. This provides for faster rescue of more people. Another factor can include the proximity to a road or otherwise straight-forward location for rescue. A pod 20 that is in proximity to a road that can be reached in a relatively straight-forward manner will have a higher priority than a pod 20 that is more remotely located. This again provides for faster rescue of a larger number of travelers. Using the example of FIG. 16, pod A has a higher priority than pod C based on the proximity to Jones Road. Another factor is the proximity to other pods 20, with pods 20 that are grouped together having a higher priority than pods 20 that are distanced apart from others. Pods 20 that are grouped together can provide for rescue of a larger number of travelers 140 in a short period of time.

Another factor is whether the pod 20 is in a dangerous position on the ground or water. In one example, a sensor 57 determines the orientation of the pod 20. If the pod 20 is inverted, additional injuries may occur to the travelers 140 than in a pod 20 that is in an upright position. A pod 20 in a dangerous position can have a higher priority for rescue.

The priority for cargo container 141 can include the same or different factors. One factor includes a hazmat rating of the cargo containers 141. A higher hazmat rating has a higher priority than a lower hazmat rating to prevent the content of the cargo containers 141 from leaking into the environment. Another factor is the distance of the pod 20 from a water source. This factors the prevention of a spill into a waterway. Another factor can be the cost of the cargo container 141 with more expensive cargo container 141 having a higher priority. Other factors can include the proximity to a road having a higher priority and the proximity to other pods 20 also having a higher priority.

The server 60 can also maintain the expected time at which emergency personnel will reach each of the pods 20. This can be based on the location of the pods 20, and the location of the emergency personnel that are working towards reaching the pods 20. The emergency personnel can periodically send updated information to the server 60 to maintain the accuracy of the expected time to rescue.

Figure 18:
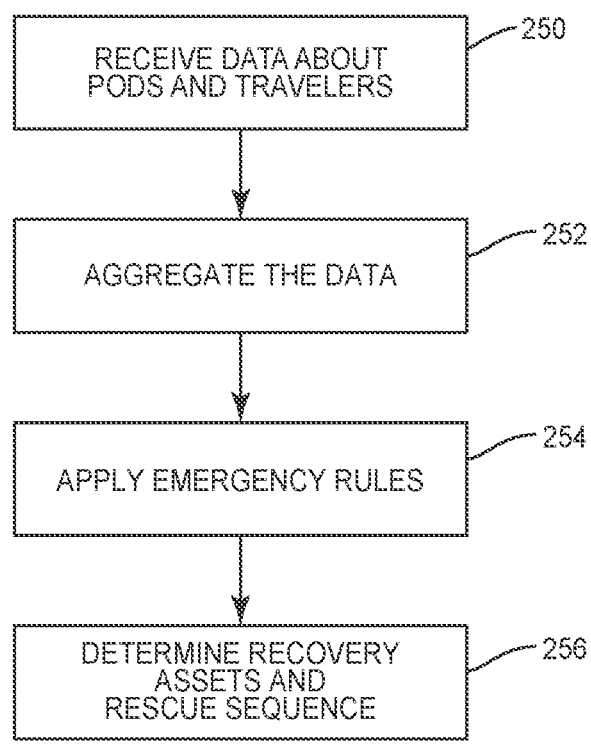
FIG. 18 is a flowchart diagram of a method of processing information by a server 60 a recovery of one or more travelers and cargo containers.

FIG. 18 illustrates a method of processing information by a server 60 for a recovery of one or more travelers 140 and cargo containers 141. The server 60 receives data about one or more of the pods 20 and travelers 140 (block 250). The data can include position and structural data about the pod 20. This data is transmitted from the one or more sensors 57 on the pod 20. Data includes but is not limited to pod identification, GPS position, structural health/integrity of the pod 20, structural damage, orientation, and whether the pod 20 has landed in water. Data can also include information about the one or more travelers 140, including but not limited to number of travelers 140, and the health condition of each traveler 140. The information can be obtained from one or more of the pods 20, vehicle 40, and previously-stored data in the database 64. Data can also be obtained from one or more sources through the PDN 71, including but not limited to weather, roads, and geography.

The server 60 aggregates the information (block 252). Rules that are stored in the memory circuit 62 are applied to the data to obtain aspects of the rescue operation (block 254). These aspects can include one or more of the rescue sequence for the pods 20 and the amount of assets needed for the recovery operation (block 256). This information can be transmitted to one or more emergency personnel, or can be maintained at the server 60 for access by rescue personnel.

Figure 19:
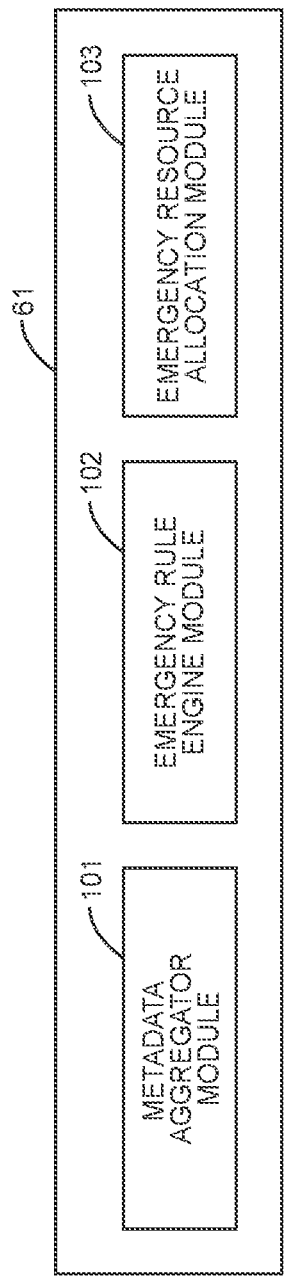
FIG. 19 is a schematic diagram of functional modules in a processing circuit of a server.

FIG. 19 includes the processing circuit 61 of the server 60 that is configured to perform various functions for the rescue operation. The processing circuit 61 includes a meta data aggregator module 101 that aggregates the data that is obtained from the pod 20 and outside sources. An emergency rule engine module 102 applies rules that are stored in the memory circuit 62 to obtain the aspects needed for the rescue operation. The rules can be default settings, or can be customizable to adjust different aspects, such as the prioritization of rescue. An emergency resource allocation module 103 determines a number of assets that are needed to perform the recovery operation. In another example, the modules 101, 102, 103 can be stored in the memory circuit 62 and accessed by the processing circuit 61 to perform the functions.

The server 60 performs these operations in a real-time manner to expedite the recovery operation and rescue of the travelers 140. The server 60 begins the processing upon determining the occurrence of a deployment of a pod 20 from a vehicle 40. This can include during the actual deployment as the one or more pods 20 exit the vehicle 40 and are moving towards a final landing location. The processing continues while the pods 20 are at the landing location to maintain the information updated to facilitate and expedite the recovery process and safety of the travelers 140.

The number of pods 20 involved in the recovery operation can vary depending upon the application. A recovery operation can include a single pod 20 that deploys from a vehicle 40. Other operations can include multiple pods 20 that are deployed from one or more vehicles 40.

In one example, the pod 20 is configured to periodically transmit location information after landing on the ground/water. The transmissions can include various information about the pod 20, travelers 140, and cargo containers 141. The transmission can also include an emergency locator beacon to assist emergency personnel in locating the pod 20.

The present invention may be carried out in other ways than those specifically set forth herein without departing from essential characteristics of the invention. The present embodiments are to be considered in all respects as illustrative and not restrictive, and all changes coming within the meaning and equivalency range of the appended claims are intended to be embraced therein.

What is claimed is:

1. A method of monitoring transportation of one or more of travelers and cargo containers in pods that are being transported on a vehicle, the method comprising:
   determining that the pods have been deployed from the vehicle;
   determining a location of the pods after landing;
   signaling the pods through communication circuitry on the pod to determine a health of the one or more travelers;
   after being unable to communicate with the one or more travelers through the communication circuitry, determining the health of the one or more travelers based on detected movement and sound within the pod;
   determining a higher medical condition severity upon detecting no movement or sound is detected after the pod has landed;
   determining a lower medical condition severity upon detecting at least one of the movement and the sound after the pod has landed; and
   transmitting to rescue personnel the location of the pods and the health of the one or more travelers.

2. The method of claim 1, further comprising prioritizing an order of rescue of the pods based on the location of the pods and the health of the one or more travelers.

3. The method of claim 2, further comprising prioritizing the order of rescue of the pods based on geographic information about the location of the pods accessed from a source through a wireless communication network in combination with the health of the one or more travelers.

4. The method of claim 1, further comprising receiving signals indicating a carbon dioxide level within the pod from the one or more sensors in the pod and determining the health of the travelers in the pods based on the carbon dioxide level relative to the number of travelers in the pod and a size of an interior space of the pod based on a position of wall segments within the pod.

5. The method of claim 4, wherein one of the signals from the one or more sensors comprises health information received through fitness equipment that is worn by one of the travelers.

6. The method of claim 1, further comprising contacting a power company through a wireless communication network and causing power to be disabled at the location prior to the pods landing at the location.

7. The method of claim 1, further comprising transmitting a location of the pods to the other pods after the pods have landed.

8. The method of claim 1, further comprising continuously monitoring the health of the travelers within the pods after the pods have landed.

9. The method of claim 1, further comprising determining one or more cargo containers within the pod contain hazardous materials and creating a rescue priority for the cargo containers with the one or more cargo containers having the hazardous materials being higher on the rescue priority than cargo containers without the hazardous materials.

10. A system to monitor transportation of one or more of travelers and cargo containers in pods that are being transported on a vehicle, the system comprising:
a plurality of pods that each comprise an interior space to house one or more of the travelers, one or more sensors that detect carbon dioxide within the interior space of the pod to determine breathing of the one or more travelers, the pods configured to attach to and be carried by the vehicle; and
a server located remotely from the pods and configured to monitor the pods, the server comprising a communication circuit and a processing circuit, the server configured to:
receive signals from the pods through a wireless communication network after the pods have been deployed from the vehicle during transportation;
communicate with the one or more travelers after landing;
determine a health of the travelers in the pods based on a detected amount of carbon dioxide in the pod relative to a number of the travelers within the pod and a size of the interior space of the pod based on positioning of wall segments within the pod when unable to communicate with the one or more travelers after the landing;
determine a location of the pods after the landing; and
transmit the information and the location of the pods to remote third parties to facilitate a rescue operation.

11. The system of claim 10, further comprising one or more canopies attached to each of the pods, the canopies comprising an undeployed orientation when the pods are attached to the vehicle and a deployed orientation when the pods have been deployed from the vehicle.

12. The system of claim 10, wherein the server is further configured to contact a power company that supplies a utility to prevent the utility from being supplied to the location while the pods are descending from the vehicle to the location.

13. The system of claim 10, wherein the server if further configured to prioritize an order of rescue for the pods based on the health of the travelers.

14. The system of claim 10, wherein the server is further configured to access information through a wireless communication network to determine one or more aspects about the location of the pods.

15. The system of claim 10, further comprising the server configured to access travel records of the pods and determining that one or more of the travelers has a pre-existing health issue.

16. A system to monitor transportation of one or more travelers and cargo containers, the system comprising:
a plurality of pods that each comprise an enclosed interior space to house one or more travelers and cargo containers, the pods configured to attach to and be carried by a vehicle;
a plurality of sensors on each of the pods configured to detect sound and movement conditions within the interior space;
a server located remotely from the pods, the server configured to:
receive signals from the pods through a wireless communication network after the pods have been deployed from the vehicle;
determine a status of the pods after the pods reach a landing location, the status of the pods comprising a geographic location of the pods, and a number of travelers in the pods; and
when unable to communicate with the one or more travelers after reaching the landing location, the status further comprising determining a higher health condition severity when no sound or movement is detected by the plurality of sensors and determining a lower health condition severity when sound and movement is detected by the plurality of sensors; and
determine a rescue priority order for the pods based on the status of the pods.

17. The system of claim 16, wherein the server is configured to be accessed by emergency personnel to access the status of the pods.

18. The system of claim 16, wherein the status of the pods further comprises an expected amount of time for emergency personnel to reach the pods.

19. The system of claim 16, wherein the server is communicatively coupled to the pods through the wireless communication network.

20. The system of claim 16, wherein the sensors are further configured to detect an amount of carbon dioxide in the pod and the server configured to determine the health of the travelers in the pod based on the amount of carbon dioxide in the pod relative to the number of travelers in the pod and a size of an interior space of the pod.

* * * * *